United States Patent [19]

Smith

[11] 4,118,416

[45] Oct. 3, 1978

[54] 5-OXA-13,14-DIDEHYDRO-PGF$_1$ COMPOUNDS

[75] Inventor: Herman W. Smith, Kalamazoo, Mich.

[73] Assignee: The Upjohn Company, Kalamazoo, Mich.

[21] Appl. No.: 776,554

[22] Filed: Mar. 7, 1977

Related U.S. Application Data

[62] Division of Ser. No. 657,739, Feb. 13, 1976, Pat. No. 4,029,681.

[51] Int. Cl.$^2$ .......................................... C07C 177/00
[52] U.S. Cl. .................................... 562/503; 560/121
[58] Field of Search ................... 260/514 D; 560/121

[56] References Cited

PUBLICATIONS

Fried et al., Proc. Nat. Acad. Sci. 70,1579 (1973).

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

53 Claims, No Drawings

5-OXA-13,14-DIDEHYDRO-PGF₁ COMPOUNDS

The present application is a divisional application of Ser. No. 657,739, filed Feb. 13, 1976, now issued as U.S. Pat. No. 4,029,681 on June 14, 1977.

The present invention relates to prostaglandin analogs for which the essential material constituting a disclosure therefor is incorporated by reference here from U.S. Pat. No. 4,029,681, issued June 14, 1977.

I claim:

1. A prostaglandin analog of the formula:

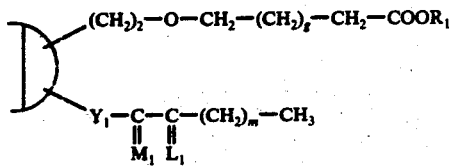

wherein D is

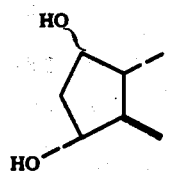

or

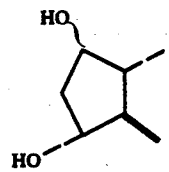

wherein $Y_1$ is —C≡C—;
wherein $g$ is 1, 2, or 3;
wherein $m$ is 1 to 5, inclusive;
wherein $M_1$ is

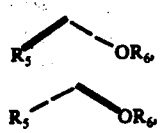

or

wherein $R_5$ and $R_6$ are hydrogen or methyl, with the proviso that one of $R_5$ and $R_6$ is methyl only when the other is hydrogen;
wherein $L_1$ is

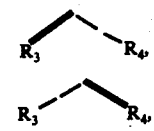

or a mixture of

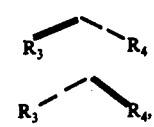

wherein $R_3$ and $R_4$ are hydrogen, methyl, or fluoro, being the same or different, with the proviso that one of $R_3$ and $R_4$ is fluoro only when the other is hydrogen; and wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

2. A compound according to claim 1, wherein D is

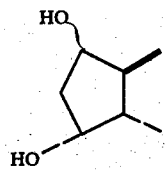

3. A compound according to claim 2, wherein $M_1$ is

and $g$ is 1.

4. A compound according to claim 3, wherein $R_3$, $R_4$, $R_5$, and $R_6$ are all hydrogen.

5. A compound according to claim 2, wherein $M_1$ is

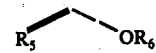

and $g$ is 1.

6. A compound according to claim 2, wherein $R_3$ and $R_4$ are both hydrogen.

7. A compound according to claim 6, wherein $R_5$ is methyl.

8. A compound according to claim 6, wherein $R_6$ is methyl.

9. 5-Oxa-13,14-didehydro-8β,12α-PGF₁α, 15-methyl ether, a compound according to claim 8.

10. A compound according to claim 6, wherein $R_5$ and $R_6$ are both hydrogen.

11. 5-Oxa-13,14-didehydro-8β,12α-PGF₁α, a compound according to claim 10.

12. A compound according to claim 2, wherein at least one of $R_3$ and $R_4$ is methyl.

13. A compound according to claim 12, wherein $R_3$ and $R_4$ are both methyl.

14. A compound according to claim 13, wherein $R_5$ is methyl.

15. 5-Oxa-15,16,16-trimethyl-13,14-didehydro-8β,12α-PGF₁α, a compound according to claim 14.

16. A compound according to claim 13, wherein $R_6$ is methyl.

17. 5-Oxa-16,16-dimethyl-13,14-didehydro-8β,12α-PGF₁α, 15-methyl ether, a compound according to claim 16.

18. A compound according to claim 13, wherein $R_5$ and $R_6$ are both hydrogen.

19. 5-Oxa-16,16-dimethyl-13,14-didehydro-8β,12α-PGF₁α, a compound according to claim 18.

20. A compound according to claim 2, wherein at least one of $R_3$ and $R_4$ is fluoro.

21. A compound according to claim 20, wherein $R_3$ and $R_4$ are both fluoro.

22. A compound according to claim 21, wherein $R_5$ is methyl.

23. 5-Oxa-15-methyl-16,16-difluoro-13,14-didehydro-8β,12α-PGF$_1$α, a compound according to claim 22.

24. A compound according to claim 22, wherein $R_6$ is methyl.

25. 5-Oxa-16,16-difluoro-13,14-didehydro-8β,12α-PGF$_1$α, 15-methyl ether, a compound according to claim 24.

26. A compound according to claim 22, wherein $R_5$ and $R_6$ are both hydrogen.

27. 5-Oxa-16,16-difluoro-13,14-didehydro-8β,12α-PGF$_1$α, a compound according to claim 26.

28. A compound according to claim 1, wherein D is

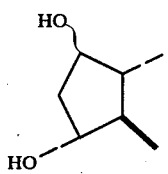

29. A compound according to claim 28, wherein $M_1$ is

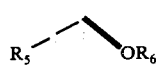

and g is 1.

30. A compound according to claim 29, wherein $R_3$, $R_4$, $R_5$, and $R_6$ are all hydrogen.

31. A compound according to claim 28, wherein $M_1$ is

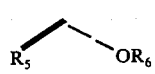

and g is 1.

32. A compound according to claim 31, wherein $R_3$ and $R_4$ are both hydrogen.

33. A compound according to claim 32, wherein $R_5$ is methyl.

34. A compound according to claim 32, wherein $R_6$ is methyl.

35. 5-Oxa-13,14-didehydro-PGF$_1$α, 15-methyl ether, a compound according to claim 34.

36. A compound according to claim 32, wherein $R_5$ and $R_6$ are both hydrogen.

37. 5-Oxa-13,14-didehydro-PGF$_1$α, a compound according to claim 36.

38. A compound according to claim 31, wherein at least one of $R_3$ and $R_4$ is methyl.

39. A compound according to claim 38, wherein $R_3$ and $R_4$ are both methyl.

40. A compound according to claim 39, wherein $R_5$ is methyl.

41. 5-Oxa-15,16,16-trimethyl-13,14-didehydro-PGF$_1$α, a compound according to claim 40.

42. A compound according to claim 39, wherein $R_6$ is methyl.

43. 5-Oxa-16,16-dimethyl-13,14-didehydro-PGF$_1$α, 15-methyl ether, a compound according to claim 42.

44. A compound according to claim 39, wherein $R_5$ and $R_6$ are both hydrogen.

45. 5-Oxa-16,16-dimethyl-13,14-didehydro-PGF$_1$α, a compound according to claim 44.

46. A compound according to claim 31, wherein at least one of $R_3$ and $R_4$ is fluoro.

47. A compound according to claim 46, wherein $R_3$ and $R_4$ are both fluoro.

48. A compound according to claim 47, wherein $R_5$ is methyl.

49. 5-Oxa-15-methyl-16,16-difluoro-13,14-didehydro-PGF$_1$α, a compound according to claim 48.

50. A compound according to claim 47, wherein $R_6$ is methyl.

51. 5-Oxa-16,16-difluoro-13,14-didehydro-PGF$_1$α, 15-methyl ether, a compound according to claim 50.

52. A compound according to claim 47, wherein $R_5$ and $R_6$ are both hydrogen.

53. 5-Oxa-16,16-difluoro-13,14-didehydro-PGF$_1$α, a compound according to claim 52.

* * * * *

UNITED STATES PATENT OFFICE
CERTIFICATE OF CORRECTION

Patent No. 4,118,416  Dated October 3, 1978

Inventor(s) Herman W. Smith

It is certified that error appears in the above-identified patent and that said Letters Patent are hereby corrected as shown below:

Column 1, lines 20-36,

" 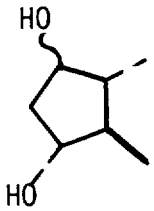 " should read -- 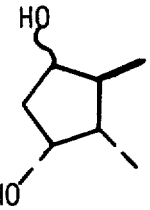 --

Signed and Sealed this

Sixth Day of March 1979

[SEAL]

Attest:

RUTH C. MASON  
*Attesting Officer*

DONALD W. BANNER  
*Commissioner of Patents and Trademarks*